United States Patent
Wilson

(10) Patent No.: US 7,684,544 B2
(45) Date of Patent: Mar. 23, 2010

(54) PORTABLE DIGITAL RADIOGRAPHIC DEVICES

(76) Inventor: Kevin S. Wilson, P.O. Box 4605, Edwards, CO (US) 81632

(*) Notice: Subject to any disclaimer, the term of this patent is extended or adjusted under 35 U.S.C. 154(b) by 0 days.

(21) Appl. No.: 11/638,431

(22) Filed: Dec. 14, 2006

(65) Prior Publication Data
US 2008/0144777 A1 Jun. 19, 2008

(51) Int. Cl.
H05G 1/10 (2006.01)
H01J 35/00 (2006.01)
H05G 1/64 (2006.01)

(52) U.S. Cl. ............... 378/102; 378/98.5; 378/119

(58) Field of Classification Search ............ 378/55, 378/91, 58–62, 98, 98.5, 98.6, 98.8, 102, 378/119, 121, 197, 210
See application file for complete search history.

(56) References Cited

U.S. PATENT DOCUMENTS

| | | | | |
|---|---|---|---|---|
| 4,646,338 A * | 2/1987 | Skillicorn | ............ | 378/110 |
| 5,077,771 A * | 12/1991 | Skillicorn et al. | ............ | 378/102 |
| 5,335,161 A * | 8/1994 | Pellegrino et al. | ............ | 363/61 |
| 5,877,501 A * | 3/1999 | Ivan et al. | ............ | 250/370.09 |
| 6,424,966 B1 * | 7/2002 | Meyerzon et al. | ............ | 707/3 |
| 6,459,767 B1 * | 10/2002 | Boyer | ............ | 378/121 |
| 6,734,880 B2 * | 5/2004 | Chang et al. | ............ | 715/738 |
| 6,754,306 B2 | 6/2004 | Cho et al. | | |
| 6,938,211 B1 * | 8/2005 | Chang et al. | ............ | 715/733 |
| 7,142,638 B2 * | 11/2006 | Polichar et al. | ............ | 378/98.8 |
| 2003/0021377 A1 * | 1/2003 | Turner et al. | ............ | 378/102 |
| 2003/0142788 A1 * | 7/2003 | Cho et al. | ............ | 378/102 |
| 2004/0015079 A1 * | 1/2004 | Berger et al. | ............ | 600/437 |
| 2004/0179651 A1 * | 9/2004 | Tong et al. | ............ | 378/98.8 |
| 2005/0105688 A1 * | 5/2005 | Spahn | ............ | 378/98.8 |
| 2005/0219242 A1 | 10/2005 | Anh et al. | | |
| 2006/0070384 A1 * | 4/2006 | Ertel | ............ | 62/3.3 |
| 2006/0098779 A1 * | 5/2006 | Turner | ............ | 378/102 |
| 2006/0110020 A1 | 5/2006 | Foos et al. | | |
| 2007/0029492 A1 * | 2/2007 | Abe | ............ | 250/370.09 |
| 2007/0140424 A1 * | 6/2007 | Serceki | ............ | 378/62 |
| 2007/0143147 A1 * | 6/2007 | Petrick et al. | ............ | 705/3 |

* cited by examiner

Primary Examiner—Edward J Glick
Assistant Examiner—Anastasia Midkiff
(74) Attorney, Agent, or Firm—Moazzam & Associates, LLC

(57) ABSTRACT

A portable handheld digital radiographic device is disclosed. The device has a touchscreen interface, an x-ray generator, and a computer system. These components are integrated into one combined device that is designed to be small, lightweight and portable.

8 Claims, 8 Drawing Sheets

PORTABLE DIGITAL RADIOGRAPHIC DEVICES

BACKGROUND OF THE INVENTION

1. Field of the Invention

The present invention relates to radiographic devices. More particularly, the present invention relates to portable X-ray generation.

2. Background of the Invention

X-ray photography has provided great benefits in the years since its introduction. X-rays are now used routinely in security settings to scan packages, luggage, and travelers for contraband. Perhaps the most visible benefit has been in the medical and veterinary fields, where x-rays are used widely, from radiation therapy to diagnostic imaging. In veterinary medicine specifically, x-rays are used to generate diagnostic images of soft tissue(s) and bone(s).

In the past, x-ray generator photography devices were bulky, unwieldy, and utilized film-cassette-chemical processor combinations to capture image data to x-ray film. In this analog style, x-ray generators emit x-rays to expose x-ray film. Exposed film is removed from the cassette housing and subjected to a chemical process, to create an x-ray image on physical film for viewing on a back-lit, light box.

Not unlike digital cameras, digital x-ray detectors have been utilized in combination with x-ray generators, to record x-ray exposure data instantly, outputting this data into a computer readable electronic format. Film-cassette-chemical processor combinations are being replaced by the digital versions.

However, such digital versions are not without their limitations. Taking up a great deal of space and weighing several hundred pounds or more, present digital x-ray devices and/or "rooms", primarily designed to be installed in a radiology suite, or for in-hospital use in fixed locations, cannot be easily moved once installed. Advances in technology have shrunk the size and weight of X-ray generators and associated digital x-ray components, to the point where "mobile" or "portable" x-ray devices on wheels or in multiple component configurations are now possible.

Yet again, even "mobile" or "portable" x-ray devices do not presently live up to the requirements of users who operate outside of a hospital environment. For example, major medical device manufacturers have developed "mobile" or "portable" hospital use digital x-ray consoles which provide for x-ray generation, digital detector capture, and computer storage/display, for use primarily at patient bedside, rather than in the radiology room suite. However, these devices still weigh, in total, approximately two hundred pounds. Two hundred pounds does not fit any reasonable definition of "portable" or "mobile" for users requiring use in the field, out of a mobile veterinary truck, in a horse's stall, in a zoo pen, or alongside a holding pen for marine mammals. Such "portable" or "mobile" devices, though more self-contained than conventional radiology suite devices, still suffer from the difficulties of portability.

Other portable x-ray generator devices, combined with the multiple separate components of a digital detector system, computer, monitor, and synchronization box, do weigh less, in total. These multi-component digital x-ray systems are used primarily in veterinary medicine for portable fieldwork in equine and zoo patients. In these multi-component solutions, several separate components work together: a portable, handheld x-ray generator; a digital x-ray detector and cable; a computer display and text input unit; and an associated "synchronization" box to coordinate the timing and functions of the individual devices. The disparate devices are coordinated using cables and are powered using several power supplies, connections, and adapters.

The conventional portable, handheld x-ray generator has a "clicker", a two-stage button. In the first stage, pressed halfway down, the clicker powers up the generator and prepares to "fire" x-ray photons. When the stand-alone x-ray generator is cabled within a team of digital acquisition devices, and the first stage of the "clicker" is activated, the first stage clicker signal is sent to a synchronization unit, which in turn communicates with a digital detector attached to the synchronization unit or attached computer. In this communication, the digital detector is communicated via the clicker-synchronization-computer chain to be in an "open" state for reception of x-rays. In the second stage, pressed fully down, the clicker commands the stand-alone generator to transmit X-rays for detection by the detector. The separate synchronization unit coordinates and synchronizes communication of timing and of data between the devices. In addition, the separate synchronization unit attached computer display has a display and keyboard (or other input device, such as a mouse, a keyboard or a touchscreen) to allow the display, process, and editing of image and patient data. These separate devices do weigh less than their "portable" or "mobile" human hospital optimized counterparts. However, they require the user to handle three to four separate components while going to and from the x-ray patient and the input and display device as the user alternates between detector positioning/exposure and image acceptance/labeling, and other functions. This problem may be especially acute in the veterinary field, where the patient, a large animal such as a horse, is out in the pasture or stable and cannot be led into an office. Further, field based exams often are performed on large, dangerous animals. By streamlining exam time and cable management, developing a new design can result in superior results, increased patient compliance, safer operation, lower costs, and superior field durability.

What is needed, therefore, is a new, integrated, portable, handheld device combining all of the features of the synchronization, display, computer processing and recording, data input, and actual x-ray generator exposure into one lightweight, portable, handheld device. In this way, users may label, expose, review, enhance, accept, and label subsequent images in a study series "patient-side," without need to interface with a stand-alone display and input computer device and synchronization unit. Further, a number of cables and power-plug-ins are eliminated, providing a more stable, smaller, safer, transportable, serviceable, and durable solution.

SUMMARY OF THE INVENTION

Conventional "portable" or "mobile" digital x-ray devices may be easier to move as compared to older generation large room x-ray machines and systems, but still do not have true portability. They remain large and bulky, often weighing up to two hundred pounds or more. Other portable digital systems that utilize a portable, handheld x-ray generator for x-ray exposure, still require multiple, separate devices, power cables, and data cables in order to provide the same functionality. The present invention addresses these problems through the development and use of a lightweight, integrated, portable handheld digital radiographic device combining the features of the synchronization/image-review unit and detector power supply unit within the x-ray generator housing.

In one exemplary embodiment, the present invention is a portable handheld digital radiographic device. The device includes an x-ray generator, a touchscreen interface coupled to said x-ray generator, and a computer system coupled to said x-ray generator. The x-ray generator, touchscreen interface, computer system, and power supply are part of a single integrated unit. The power source for the power supply may be rechargeable or permanent battery, 110 v, 220 v, or other power source.

In another exemplary embodiment, the present invention is a portable handheld digital radiographic device. The device includes an x-ray generator and a touchscreen interface. A computer system is detachably coupled to the x-ray generator. The computer system further comprises a computer readable medium containing a plurality of applications. The x-ray generator, touchscreen interface, and computer system are integrated as part of a single device.

DETAILED DESCRIPTION OF THE INVENTION

The present invention provides in certain exemplary embodiments an integrated portable handheld digital radiographic device capable of capturing, storing, and manipulating digital X-ray images and associated patient data. The present invention also takes advantage of the device's portability and integrated nature as it provides for multiple uses for various components of the device, thereby increasing efficiency. The present invention may be used in any environment where portable handheld x-ray generators are conventionally used, such as, for example, in military, security, medical, or veterinary settings.

As defined herein and throughout this disclosure, a digital radiographic device is a portable apparatus able to generate and store X-ray images for purposes of radiology, medical imaging, radiography, pathology, microscopic analysis, crystallography, or any similar field where diagnostic or experimental imaging is used. This apparatus includes an X-ray generator, positioning hardware and software to align the generator with the subject, and a storage device.

As defined herein and throughout this disclosure, an x-ray image is an image generated using electromagnetic radiation that allows visualization of objects within the external surface of the subject of the image.

Figure 1:
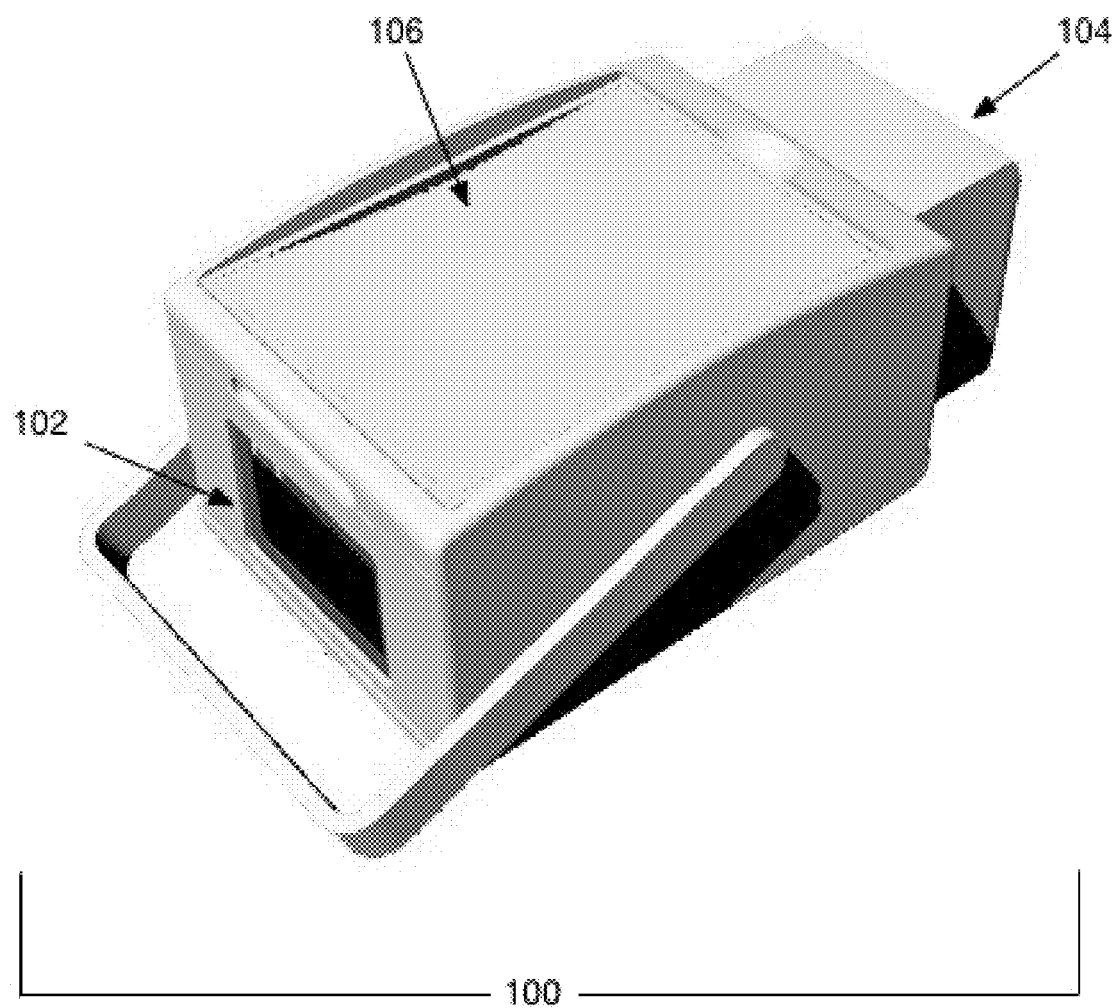
FIG. 1 shows a portable radiographic device according to an exemplary embodiment of the present invention.
Figure 8:
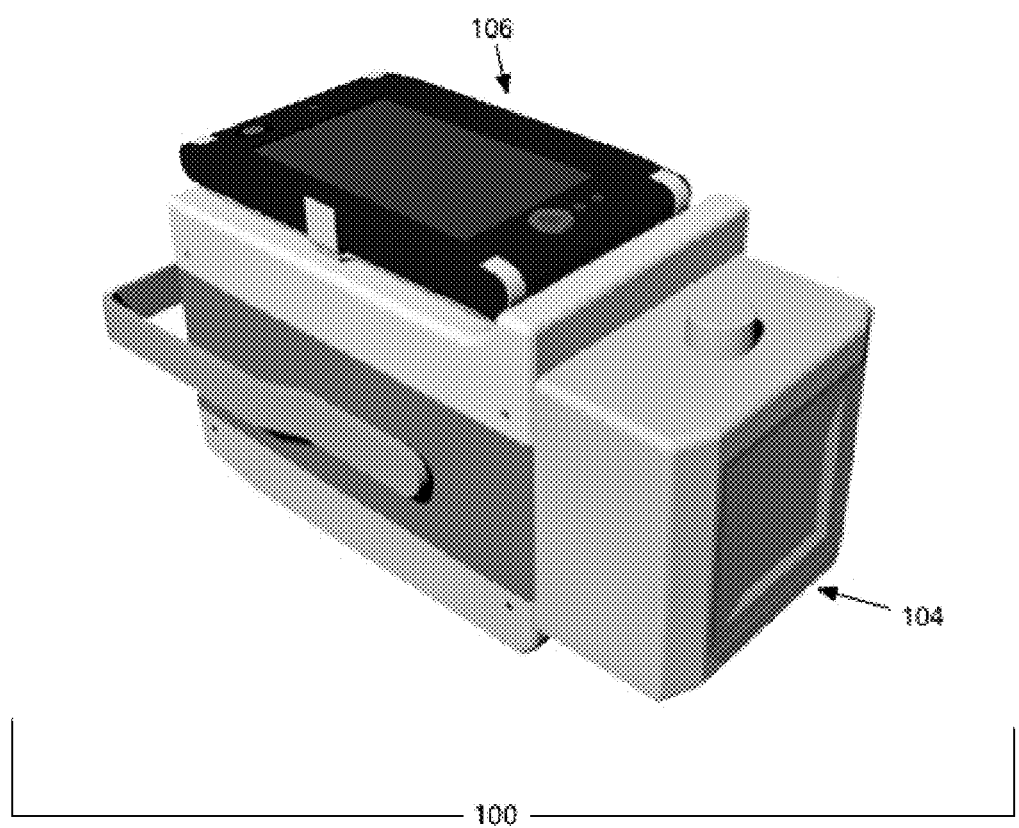
FIG. 8 shows a portable radiographic device according to another exemplary embodiment of the present invention.

A first exemplary embodiment of the present invention is shown in FIGS. 1 and 8. FIGS. 1 and 8 are two views of the first embodiment. In FIG. 1, portable radiographic device 100 has three components: x-ray generator 104, touchscreen interface 106, and computer system 102. FIG. 8 is another view of the portable radiographic device, showing the x-ray generator 104 and the touchscreen interface 106. X-ray generator 104 may be located at the front or other position of radiographic device 100. Touchscreen interface 106 may be located on the top, and computer system 102 on the back. Other locations are also possible and within the scope of the present invention. The radiographic device 100 is an integrated unit, combining both the computer system 102 and x-ray generator 104, which previously were separate and independent components. As an integrated unit, radiographic device 100 is easy to carry from place to place. Preferably, radiographic device 100 should not weigh more than about 40 pounds. The more radiographic device 100 weighs, the less portable and less useful it becomes. In terms of dimensions, radiographic device may have dimensions of 13.5 inches in width, 24.5 inches in length, and 12.5 inches in height. Other weights and dimensions are also possible and within the scope of the present invention.

Figure 2:
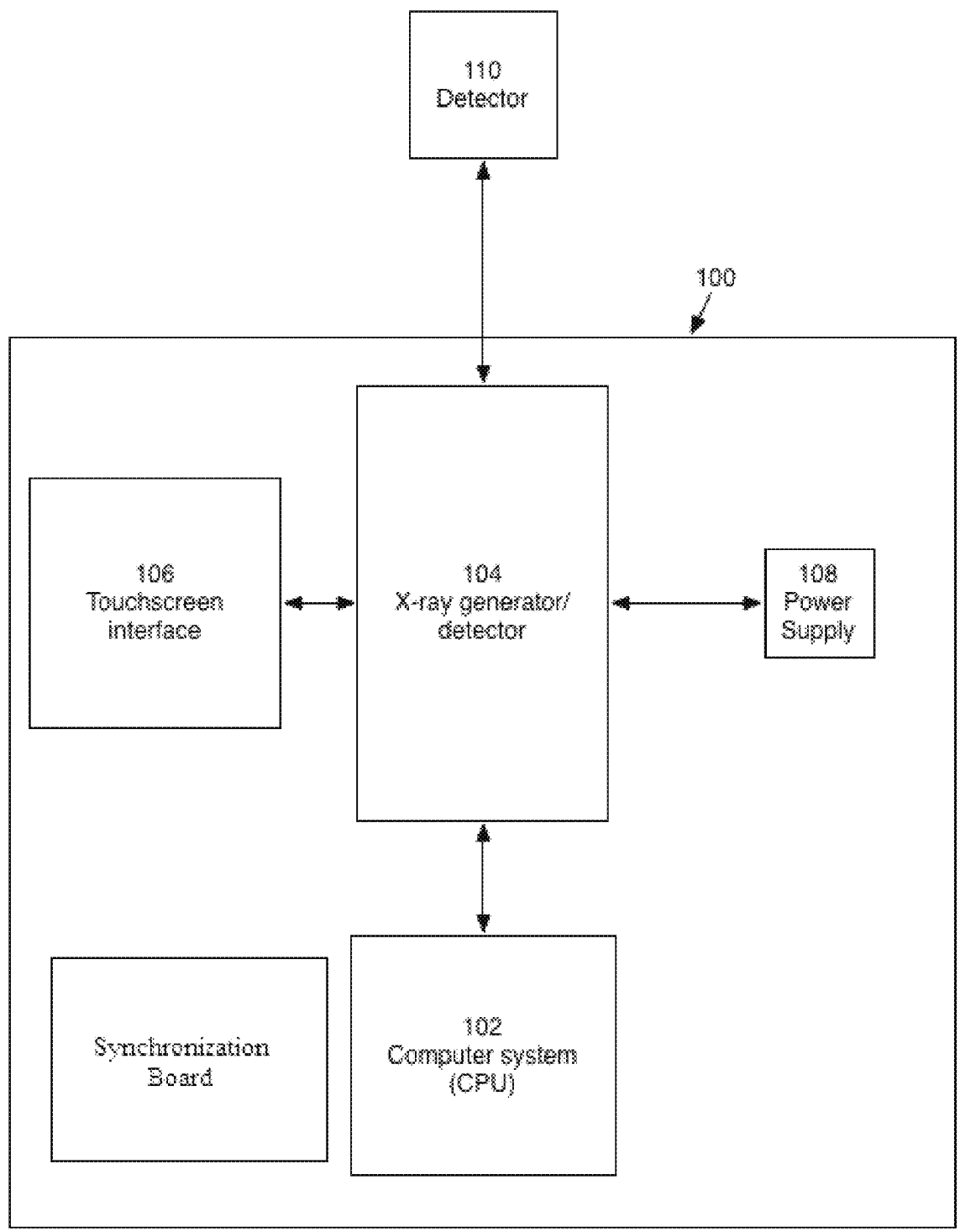
FIG. 2 shows a diagram of certain components according to an exemplary embodiment of the present invention, as well as an x-ray detector.

FIG. 2 shows a schematic diagram of an exemplary embodiment of the present invention. Touchscreen interface 106 and computer system 102 are coupled to the x-ray generator 104. Power supply 108 is also coupled to x-ray generator 104 and supplies power to radiographic device 100, including x-ray generator 104, computer system 102, and touchscreen interface 106. Touchscreen interface 106, computer system 102, and X-ray generator 104, as well as any other components, such as input devices like keyboards, and output devices such as printers, may be integrated into a single unit within radiographic device 100. This reduces a number of devices that a user must purchase and carry. Power supply 108 may also be integrated into radiographic device 100 or it may be separate, attached to radiographic device 100 via a fixed or detachable cable. Depending on the power needs of radiographic device 100, there may be one or more power devices integrated into or attached to radiographic device 100.

FIG. 2 also shows flat panel detector 110. While flat panel detector 110 is attached to radiographic device 100, radiographic device 100 acts as a digital radiography device. Flat panel detector 110 does not have to be part of radiographic device 100 and is conventionally available. Flat panel detector 110 detects the x-rays generated by x-ray generator 104 and transmits the resulting image back to radiographic device 100. Flat panel detector 110 may be connected to radiographic device 100 by way of a detachable cable. The detachable cable may be a USB, FireWire, Ethernet, combination cable including power and data capabilities, or other cable or communication route. The cable connects to radiographic device 100 via a data port on radiographic device 100. This port may be located on any convenient position on radiographic device 100 but preferably in a position where the cable can remain secure, clean and durable, and where stress on the cable can be minimized. These issues are important since the cable is likely to be detached and reattached multiple times and will be used in fieldwork conditions, such as stallside (for horses), battlefield, and security environments.

The cable may act as both a data transmission cable (via FireWire, USB1, USB2, RS-XXX, Ethernet, other data transmission cable or any equivalent data transfer protocol) as well as a power transmission cable. The flat panel detector 110 is provided with power from the radiographic device 100, via the detachable cable. Cable may be detached at the radiographic device 100, at the detector 110, anywhere in between the two originating points, or any combination thereof. The user may detach the cable from the radiographic device 100 when the flat panel detector 110 is not needed. The user may also store the cable separately from radiographic device 100. As discussed previously, flat panel detector 110 may be any flat panel detector known in the art, such as, for example, a Varian 2520, Canon CXDI-31, DR Tech FDXD-810, or similar device(s) from Thales, Trixell, Hologic, General Electric, or Perkin Elmer.

In the event flat panel detector cable is detached from radiographic device 100, radiographic device 100 may operate as a stand-alone, traditional x-ray generator camera, using the touchscreen interface 106 and/or computer system 102 to enter and initiate traditional x-ray technique information. While in this traditional mode, the radiographic device 100 may use the computer system 102 and touchscreen interface 106 to control and initiate technical presets and manual settings, including kVp, mAs, time, MA station, high frequency X-ray generator preparation, and high frequency x-ray generator x-ray emission ("exposure"). These controls may exist in either hardware or software or a combination of hardware and software controlled by Active X code or other computer readable code controls.

Radiographic device 100 includes an internal, embedded, or directly coupled synchronization circuit board. The synchronization board synchronizes the functions of x-ray generator 104, computer system 102, and flat panel detector 110 when the radiographic device is operating in digital acquisition mode. This synchronization includes synchronizing preparation, timing, opening/closing of detector "windows", x-ray emission, sequence initiation, receipt of data, and processing of both signals and data between the x-ray generator 104, computer system 102, flat panel detector 110, and any other component of radiographic device 100.

X-ray generator 104 performs x-ray imaging functions. The generator component may be attached in the main body of the device and is coupled to computer system 102 and touchscreen interface 104. The generator component 104 generates x-rays. These x-rays are absorbed at differing rates by substances having varying densities, such as bone, tumors, and other inconsistencies in the subject of the scan. A detector can pick up the resulting "shadows" cast by the substances absorbing the x-rays, generating an image of the object, person, or animal being scanned. The strength of the x-rays depends on what the operator wishes to examine. If the operator wishes to examine a bone (for example to determine if a break has occurred), the operator will use a stronger x-ray than if the operator wishes to look at softer tissue. X-ray generator 104 may be equipped to generate x-rays of any type or strength necessary. The x-ray generator may be any generator available, so long as it is relatively lightweight, such as, for example, a Min-Xray 80/15, Min-Xray 100/30, Poskom PXP-16HF, Poskom PXP-20HF, Poskom PXP40HF, or other similar x-ray generator. The lightweight requirement is needed for the x-ray device 100 to remain portable.

Touchscreen interface 106 may be attached to the top of radiographic device 100 and is coupled to computer system 102 and x-ray generator 104. Touchscreen interface 106 provides both the input and the display functions for x-ray device 100 and acts as the interface between the user and the x-ray device 100 and the computer system 102. The touchscreen is preferably a sunlight readable transflective touchscreen. Transflective touchscreens are designed to be equally readable both in sunlight and in artificial or low-light situations. Use of a transflective touchscreen allows users to operate the device outdoors or in any other environment without an artificial light source or with limited light sources. The touchscreen utilizes a graphical user interface, which may be provided by an operating system or other software stored on computer system 102. Use of a touchscreen eliminates the need for a separate display, another source of potential weight. Further, the touchscreen also eliminates the need for a separate mouse and keyboard. The operator of the device is thus not required to carry around bulky or awkward accessory components, which may be easily lost.

Touchscreen interface 106 acts as the primary user interface between the user and the device, including computer system 102. Touchscreen interface 106 allows the operator to enter patient data into PACS (Picture Archiving and Communications System) 402, shown in FIG. 4. The user can acquire an image using the touchscreen interface. The user can label the image using DICOM (Digital Imaging and Communication in Medicine) 406 annotation. The user can label the upcoming exposure, review the image, study the image, enhance the image, and accept the image through the touchscreen interface. These are examples of how the user may operate the system using the touchscreen interface. The touchscreen interface may also permit the user to interact with, and perform any other function of radiographic device 100, including for example, manually adjusting the device's radiographic technique exposure, time and power settings. Touchscreen interface 106 may be directly coupled to computer system 102, and may remain coupled to computer system 102 if computer system 102 is detached from the x-ray generator 104.

Computer system 102 is coupled to x-ray generator 104 and may be attached to the rear of radiographic device 100 (as shown in FIG. 1) or atop of the radiographic device 100. Computer system 102 may also be coupled to the touchscreen interface. This connection could be, for example, a monitor cable to communicate data directly from computer system 102 to touchscreen interface 104, or this connection may be a direct coupling of computer system 102 and touchscreen interface 106, for example, as embodied by a Samsung Q1, a Sony VAIO UX Micro-PC, or other similar micro PC or tablet PC.

Computer system 102 acts as the console for x-ray generator 104 and radiographic device 100. Computer system 102 controls the operation of x-ray generator 104. In addition, computer system 102 receives input from touchscreen 106, transmits commands to x-ray generator 104, receives x-ray images, and is able to store and manipulate data relating to the x-ray images it receives. In addition it can perform any other standard function of computers.

Computer system 102, in association with the printed circuit board/cable port synchronization of hardware and software functions coupled to the radiographic device 100 or the flat panel detector 110, also synchronizes communication between the clicker, the x-ray generator 104, the computer system 102, and flat panel detector 110. The function of the clicker may be performed by either x-ray generator 104 or by hardware or software in computer system 102. In addition, computer system 102 performs the synchronization, image reception, image review, and other functions previously accomplished by a separate synchronization and computer display. Integrating computer system 102 with x-ray generator 104 into a single radiographic device 100 reduces the overall cost of the system, increases portability, and dramatically increases speed and accuracy of study image acquisition, labeling, review, enhancement, and acceptance by moving those and other functions "patient-side" in one integrated device.

Figure 3:
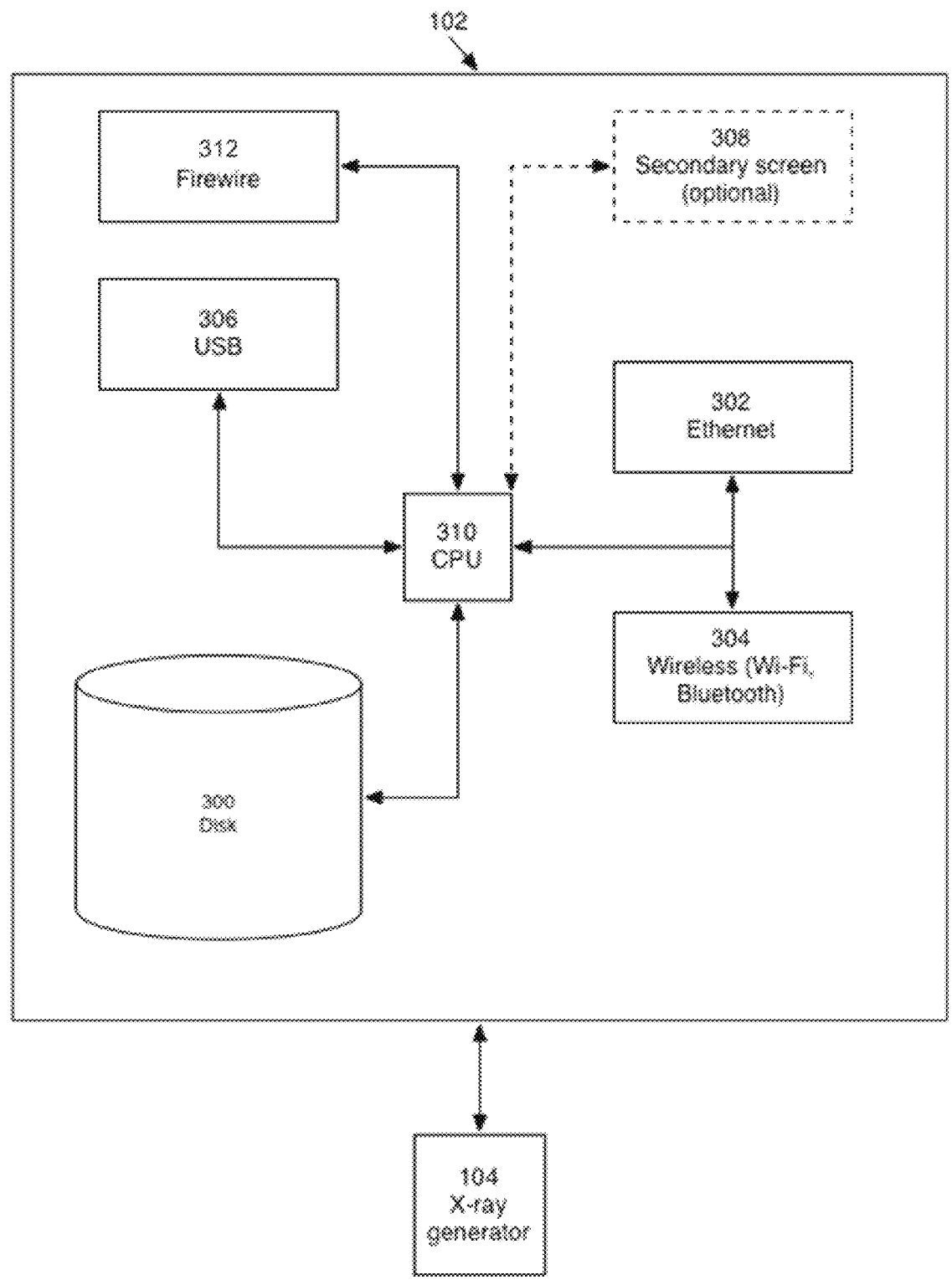
FIG. 3 shows a diagram of a computer system according to an exemplary embodiment of the present invention.

FIG. 3 shows an exemplary embodiment of computer system 102. Computer system 102 contains any components standard for computers, including a central processing unit (CPU) 310, hard disk 300, video card, and random-access memory (RAM). Computer system 102 may also have networking components, such as an Ethernet component 302 and/or wireless component 304. Wireless component 304 may employ any wireless communication standard, including BLUETOOTH and Wi-Fi (IEEE 802.11x) or any equivalent current or future wireless protocol. In addition, computer system 102 may have USB port 306 and Firewire (IEEE 1394) port 312. The USB port 306, Ethernet component 302 and Firewire port 312 permit radiographic device 100 to communicate with outside and peripheral devices. Computer system 102 may include a removable media drive, such as a CD-ROM or DVD drive. Computer system 102 may also be equipped with voice-recognition technology and/or audible voice guided image label protocols, wherein the device audibly notifies the user of the next image in a series to be automatically labeled and then acquired by the user. Computer system 102 contains other components normally found in conventional computer systems, but such components have not been shown in FIG. 3 for sake of simplicity.

Figure 4:
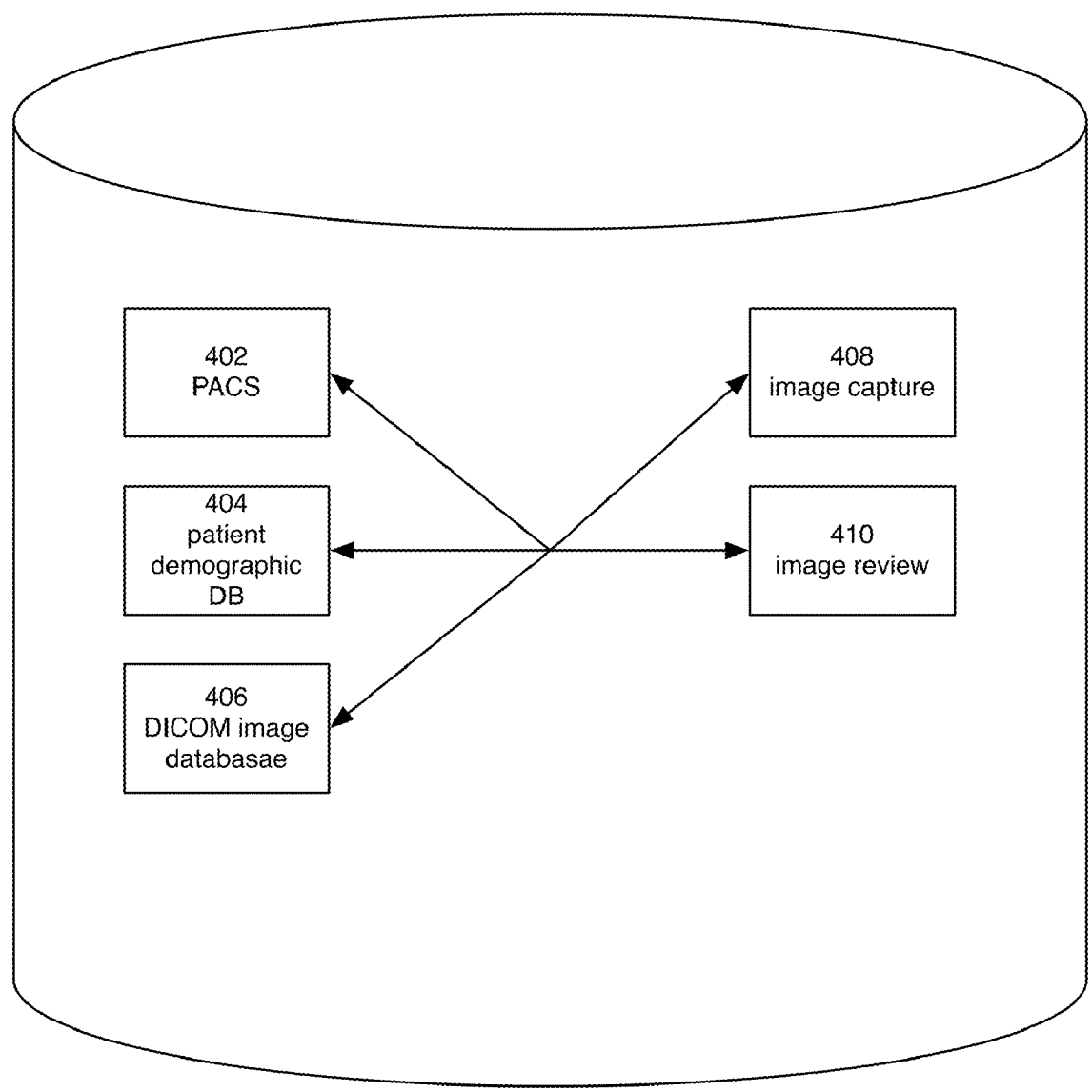
FIG. 4 shows various software components that may be included in the computer system according to an exemplary embodiment of the present invention.

Computer system 102 may be any suitable computer system, for example, a Sony VGN-UX280 P micro PC or a Samsung Q1 computer. Computer system 102 may run on any operating system, such as Linux, Mac OS, or Microsoft™ Windows™. The operating system is stored on hard disk 300 along with other software used by computer system 102. FIG. 4 shows examples of such software stored on the hard disk 300. In addition, computer system 102 may include software for operating x-ray generator 104 as well as other components of radiographic device 100. This software may comprise ActiveX controls, which may control all standard x-ray generator settings, including kVp, mAs, Time, MA Station, high frequency x-ray generator preparation, and high frequency x-ray generator x-ray emission.

A useful component of the software included on computer system 102 is PACS 402. PACS 402 is a Picture Archiving and Communication System. A full-scale PACS is designed to operate over a network, to take in images and data from multiple sources, and provide workflow solutions. A full PACS can handle the needs of an entire hospital. For the purposes of the present disclosure, a small-scale, or "mini" PACS may be used. The PACS 402 obtains images and permits the user to manipulate, mark, identify, and store the images in an image database, such as DICOM image database 406. The PACS utilizes image capture software 408 and image review software 410 to capture images and to permit a user to review the images. Image capture software 408 will capture the images using Raw data, JPEG, Bitmap, TIFF, and/or any format incorporated into the DICOM standard, a standard format in the medical field. If necessary, the user may edit images captured with image capture software 408 using image capture software 408, image review software 410, or PACS 402. In addition to these components, PACS 402 may also include a patient archive, image optimization, image enhancement, defect correction, and appropriate DICOM classes.

Images captured using PACS 402 and/or image capture software 408 may be stored in DICOM image database 406. DICOM refers to "Digital Imaging and Communications in Medicine". DICOM is a set of standards for handling, storing, printing, and transmitting medical images, such as the x-ray images created by the radiographic device 100. The DICOM image database 406 uses the storage capabilities to store images captured using the PACS 402/image capture software 408 until such time as the images may be permanently stored in an outside archiving device. DICOM image database 406 may also serve as the permanent storage for images if no other outside device serves that function.

Computer system 102 may also have a patient demographic database (DB) 404. Patient demographic database 404 may store information about patients not stored in other parts of the system (such as DICOM image database 406), but that a user may need to have access to while reviewing images captured using x-ray device 100.

In one exemplary embodiment, PACS 402 displays three main screens: Archive, Acquire, and Review. The Archive area stores information about patients who have had x-rays taken. The information may include the patient's name, a patient ID, the patient's age, the client's last name (since the patient and the client may be different, especially in the veterinary field), species (important information in the veterinary field), weight, and birth date. The particular information provided can vary depending on the intended use of the system. For example, PACS 402 may automatically fill in the species field with "Human" for medical use; in addition, when being used for medical purposes, PACS 402 may also hide the species field since all the patients will be human. The Archive screen may also have an on-screen keyboard to facilitate data entry. The Archive screen also offers the ability to upload information to a remote server, clear one or more fields, create new patient entries, view an existing entry in greater detail, and proceed to acquire images. The Archive screen may also include any other functionality useful for patient data review and archival purposes.

The Acquire screen is the interface for acquiring the image and making any initial changes to the image. The Acquire screen may take advantage of secondary screen 308. Touchscreen interface 106 displays the acquired image. The operator can examine the image to see if it is acceptable. If the operator wishes to take another exposure or to alter the current one, controls shown on the Touchscreen interface 106 and/or the secondary screen 308 permit the user to do so. The Acquire screen may offer some ways to edit the image, including brightening or darkening it. Using the Acquire screen, the user can retake the image, move to the next image in a series, or move to a different screen. The Acquire screen utilizes the Touchscreen interface 106 to label each image in a study with corresponding data, including anatomy, laterality, and view for capture into the image data file. The Acquire screen permits the user to control the view, anatomy, and laterality of the shot being taken by X-ray generator 104. In addition, the Acquire screen permits the user to control operation of the X-ray generator, including the exposure time, power, mAs (milliamps), and kVp (kilovolt peak).

The Review screen permits the operator to review the image acquired by the x-ray generator 104. The image, as well as information about the image, is displayed on touchscreen interface 106. The review screen may also display any other information useful to the operator when reviewing an image. Image review controls permit the operator to save the image, as well as to manipulate the image in certain ways, such as flip, reverse, rotate, move, zoom (in or out), and revert. Image review controls may include any control useful when reviewing an image.

FIG. 4 shows the PACS 402, patient demographic database 404, DICOM image database 406, image capture software 408, and image review software 410 as separate components. However, depending on the implementation, one or more of patient demographic database 404, DICOM image database 406, image capture software 408, or image review software 410 may be a sub-component of PACS 402. PACS 402 may use any implementation available in the art without departing from the present invention. Previous x-ray generators did not include PACS. Radiographic device 100 integrates PACS 402 with x-ray generator 104, giving the user full access to PACS 402 without the need for an outside device. In another exemplary embodiment, computer system 102 has a secondary screen 308, which can be used for secondary purposes. Secondary screen 308 is shown by dotted lines in FIG. 3. The secondary screen may also be a touchscreen interface to allow the operator to control operation of radiographic device from secondary screen 308. For example, when reviewing an image the image itself could appear on the touchscreen interface 106, while the manipulation controls (rotate, flip, zoom, etc.) can appear on the secondary screen 308 so as to provide more display space on the touchscreen for the image itself.

PACS 402 may take advantage of the secondary screen 308 by moving some functions from touchscreen interface 104 to secondary screen 308. On the Acquire screen, x-ray generator controls may appear on the secondary screen 308. The user can control the strength of the x-rays generated by x-ray generator 104. The user may also control the exposure time, power, mAs (milliamps) and kVp (kilovolt peak). In addition, the Acquire screen on secondary screen 308 can control the view, anatomy, and laterality of the shot being taken by the x-ray generator 104. The Acquire screen may also include any control or feature useful when acquiring x-ray images, to be displayed and interacted with by the user on the Touchscreen interface 106 and/or the secondary screen 308. On the Review screen, image review controls may be located on the secondary screen 308 so as to maximize the amount of space on the touchscreen interface 106 for displaying the image.

Figure 5:
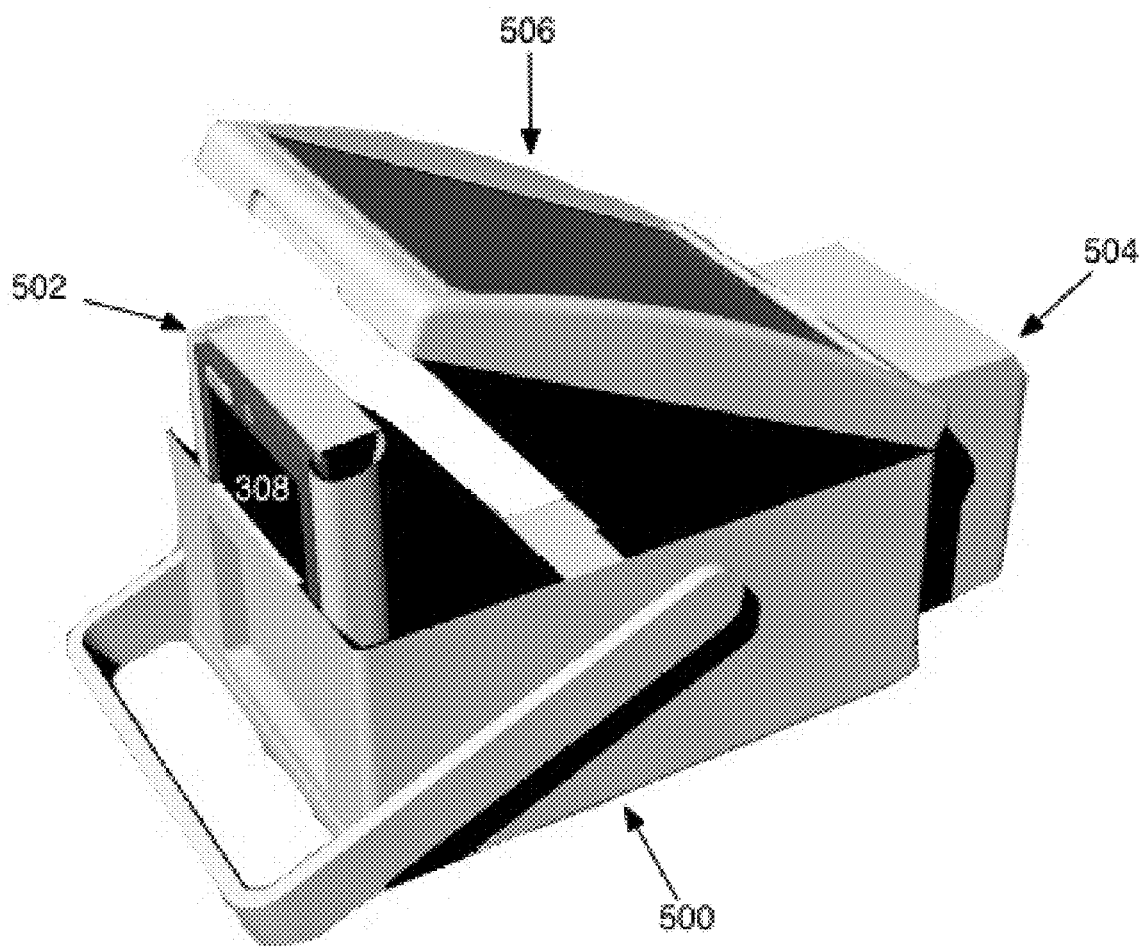
FIG. 5 shows a portable radiographic device according to another exemplary embodiment of the present invention.
Figure 6:
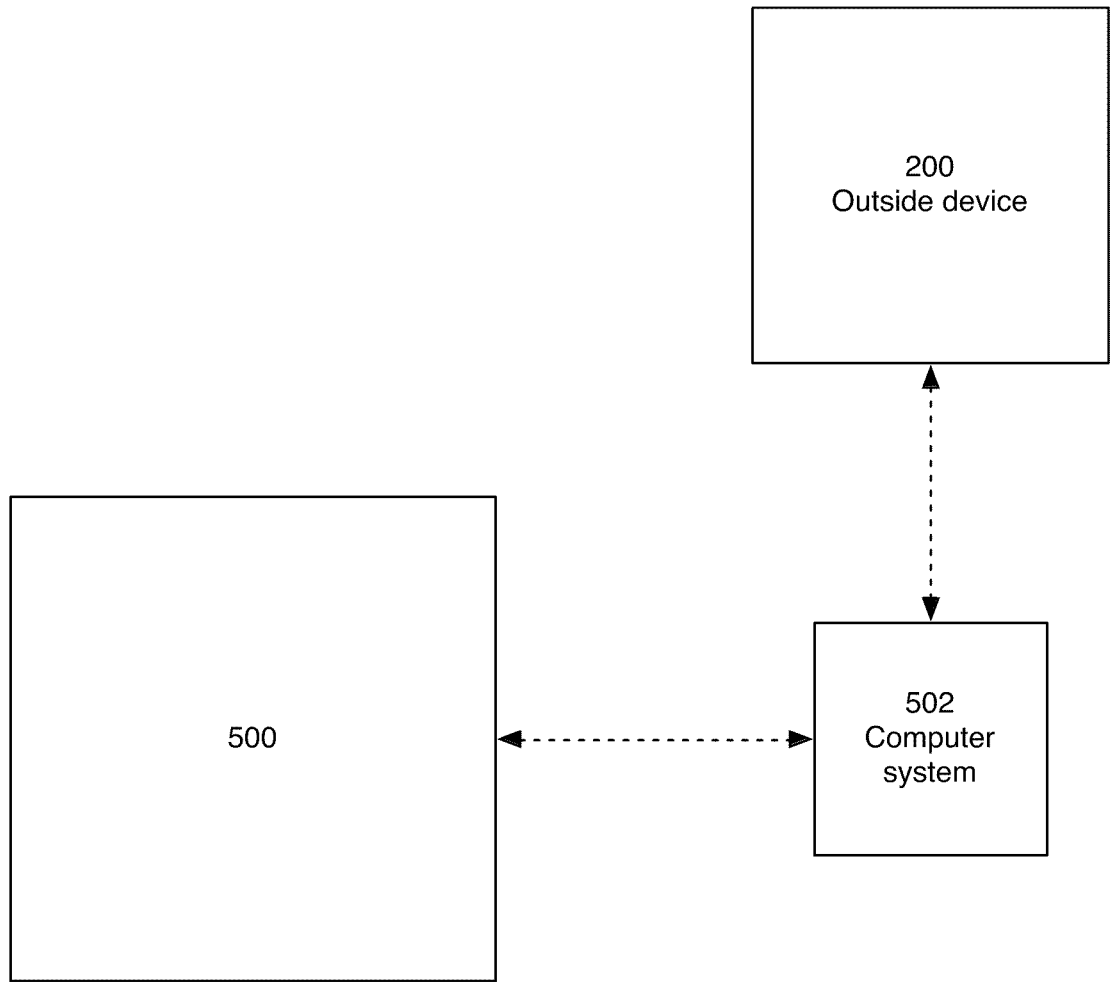
FIG. 6 shows a diagram of a computer system removed from a radiographic device according to an exemplary embodiment of the present invention.
Figure 7:
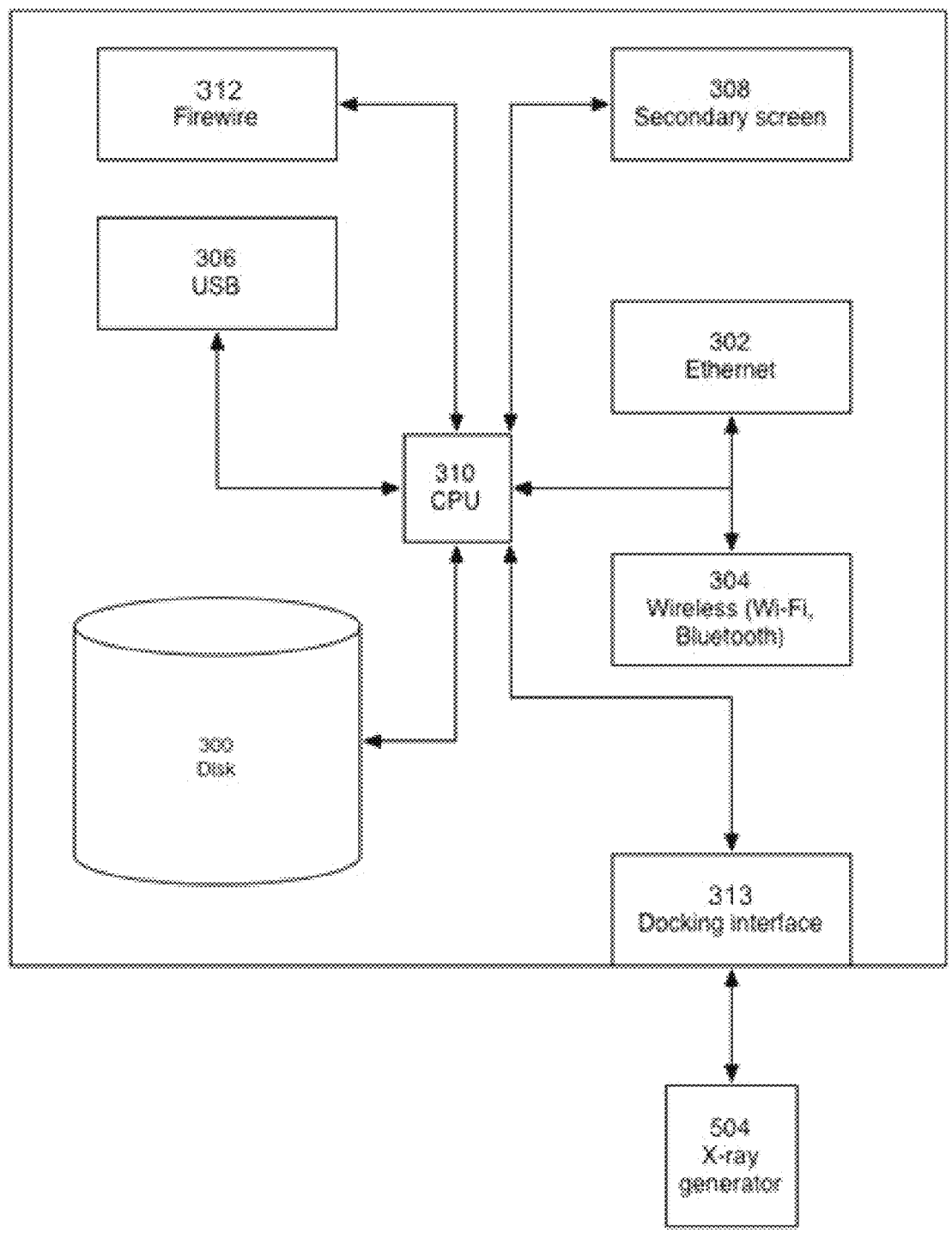
FIG. 7 shows various components of a computer system according to an exemplary embodiment of the present invention.

A third exemplary embodiment of the present invention is shown in FIGS. 5, 6, and 7. In this particular embodiment, shown in FIG. 5, computer system 502 is detachably coupled to the other components of the device. Touchscreen interface 504 may tilt upwards to allow access to the interior of radiographic device 500 and to permit the removal of computer system 502. Once computing system 502 has been removed from radiographic device 500, as shown in FIG. 6, computing system 502 can dock to an outside device 200. Outside device 200 may perform archival, storage, and other functions not needed to operate radiographic device 500, but which may be helpful for future reference, diagnosis, or other purposes. Outside device 200 could also be a full-resolution (at least 1024×768) monitor. A large, full resolution monitor permits the operator to examine the x-ray images more closely than the touchscreen interface would, enhancing the diagnostic and medical usefulness of the device. The ability to detach computer system 502 gives the user the "best of both worlds." When the user needs an integrated system, such as out in the field, the components are integrated; when the user no longer needs an integrated system, such as back in the office, the computer system may be detached and used separately.

The computing system 502 according to this exemplary embodiment has all of the features of the computing system 102 according to the first exemplary embodiment described above. Computer system 502 according to the present invention has additional features as well. These additional features include docking interface 313. Docking interface 313 allows computer system 502 to undock from radiographic device 500. Docking interface 313 may also be used to dock with outside devices 200, such as an archival/storage device or a high-resolution monitor.

Regardless of embodiment, radiographic device 100 may come in a durable, compact, lightweight, attractive storage case. The storage case can store the radiographic device and any detachable components, power cables, detectors, cables, external drives, recordable media, hand "clicker", and any other accessories that might be needed in the field. All in all, the entire system may be contained within a suitcase size package and weigh in at a total of up to about 35 to 40 pounds. This would make the present invention portable in virtually any environment in which an x-ray on site would be highly desirable.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A portable digital radiographic device, comprising:
   an x-ray generator;
   a first touchscreen interface coupled to said x-ray generator for control by a user;
   a second touchscreen interface, separate from the first touchscreen interface, and coupled to said x-ray generator for displaying images;
   a computer system detachably coupled to said x-ray generator and further comprising a computer readable medium containing a plurality of applications; and
   a synchronization circuit board operative to synchronize the operation of the x-ray generator, and the computer system;
   wherein the x-ray generator, first and second touchscreen interfaces, synchronization circuit board, and computer system are part of a single unit.

2. The device of claim 1, wherein one of said plurality of applications is a PACS (picture, archival, communications software).

3. The device of claim 2, wherein the PACS contains at least one of a patient demographic database, image capture software interface, DICOM image database, and image review software.

4. The device of claim 2, wherein the PACS performs archive, acquiring, labeling, image sorting, and review functions.

5. The device of claim 1, wherein the second touchscreen interface instantly displays image data received from an x-ray detector.

6. The device of claim 1, wherein the first touchscreen interface controls operation of said computer system.

7. The device of claim 1, wherein the first touchscreen interface controls operation of the x-ray generator, including at least one of exposure time, power, mAs, and kVp.

8. The device of claim 1, wherein the computer system controls operation of said x-ray generator via at least one ActiveX control.

* * * * *